United States Patent
Nagy

(10) Patent No.: US 6,210,312 B1
(45) Date of Patent: Apr. 3, 2001

(54) CATHETER AND GUIDE WIRE ASSEMBLY FOR DELIVERY OF A RADIATION SOURCE

(75) Inventor: John S. Nagy, Marina del Rey, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 08/859,217

(22) Filed: May 20, 1997

(51) Int. Cl.$^7$ .................................................... A61N 5/00

(52) U.S. Cl. ....................................................... 600/3; 600/8

(58) Field of Search ............................. 600/1–8; 604/93, 604/96

(56) References Cited

U.S. PATENT DOCUMENTS

| | | |
|---|---|---|
| 4,323,071 | 4/1982 | Simpson et al. . |
| 4,439,185 | 3/1984 | Lundquist . |
| 4,468,224 | 8/1984 | Enzmann et al. . |
| 4,538,622 | 9/1985 | Samson et al. . |
| 4,554,929 | 11/1985 | Samson et al. . |
| 4,581,017 | 4/1986 | Sahota . |
| 4,582,181 | 4/1986 | Samson . |
| 4,616,652 | 10/1986 | Simpson . |
| 4,638,805 | 1/1987 | Powell . |
| 4,661,094 | 4/1987 | Simpson . |
| 4,697,575 | 10/1987 | Horowitz . |
| 4,706,652 | 11/1987 | Horowitz . |
| 4,744,366 | 5/1988 | Jang . |
| 4,748,982 | 6/1988 | Horzewski et al. . |
| 4,748,986 | 6/1988 | Morrison et al. . |
| 4,762,130 | 8/1988 | Forgarty et al. . |
| 4,763,671 | 8/1988 | Goffinet . |
| 4,771,777 | 9/1988 | Horzewski et al. . |
| 4,771,778 | 9/1988 | Mar . |
| 4,775,371 | 10/1988 | Mueller, Jr. . |
| 4,790,315 | 12/1988 | Mueller, Jr. et al. . |
| 4,815,449 | 3/1989 | Horowitz . |
| 4,827,941 | 5/1989 | Taylor et al. . |
| 4,861,520 | 8/1989 | van't Hooft et al. . |
| 4,898,577 | 2/1990 | Badger et al. . |
| 4,936,823 | 6/1990 | Colvin et al. . |
| 4,940,064 | 7/1990 | Desai . |
| 4,969,863 | 11/1990 | van't Hooft et al. . |
| 4,976,720 | 12/1990 | Machold et al. . |
| 4,983,167 | 1/1991 | Sahota . |
| 4,994,560 | 2/1991 | Kruper, Jr. et al. . |

(List continued on next page.)

FOREIGN PATENT DOCUMENTS

| | | |
|---|---|---|
| 9102312 | 2/1991 | (DE) . |
| 4315002 | 5/1993 | (DE) . |
| 0633041 | 7/1993 | (EP) . |
| 0688580 | 6/1994 | (EP) . |
| 0 633 041 | 1/1995 | (EP) . |

(List continued on next page.)

OTHER PUBLICATIONS

Stuart Lindsay et al., "Aortic Arteriosclerosis in The Dog After Localized Aortic X–Irradiation", Circulation Research, vol. X, pp 51–60, Jan. 1962.

Meyer Friedman et al., "The Antiatherogenic Effect of Iridium$^{192}$ Upon the Cholesterol–Fed Rabbit", Journal of Clinical Investigation vol. 43, No. 2, pp 185–192, 1964.

Meyer Friedman et al., "Effect of Iridium$^{192}$ Radiation on Thromboatherosclerotic Plaque in the Rabbit Aorta", Arch Path vol. 80, pp 285–290, Sep. 1965.

(List continued on next page.)

Primary Examiner—Jeffrey R. Jastrzab
(74) Attorney, Agent, or Firm—Blakely, Sokoloff, Taylor & Zafman

(57) ABSTRACT

A guide wire for use in intravascular procedures having a proximal hollow portion and a solid distal portion. The hollow portion is adapted to receive a radioactive source for irradiating a body lumen to reduce the likelihood of the development of restenosis.

81 Claims, 4 Drawing Sheets

U.S. PATENT DOCUMENTS

| | | |
|---|---|---|
| 4,998,917 | 3/1991 | Gaiser et al. . |
| 5,002,560 | 3/1991 | Machold et al. . |
| 5,015,230 | 5/1991 | Martin et al. . |
| 5,019,042 | 5/1991 | Sahota . |
| 5,032,113 | 7/1991 | Burns . |
| 5,034,001 | 7/1991 | Garrison et al. . |
| 5,040,543 | 8/1991 | Badera et al. . |
| 5,046,503 | 9/1991 | Schneiderman . |
| 5,050,606 * | 9/1991 | Tremulis ............................ 128/637 |
| 5,059,166 | 10/1991 | Fischell et al. . |
| 5,061,273 | 10/1991 | Yock . |
| 5,084,002 | 1/1992 | Liprie . |
| 5,100,429 | 3/1992 | Sinofsky et al. . |
| 5,133,956 | 7/1992 | Garlich et al. . |
| 5,137,513 | 8/1992 | McInnes et al. . |
| 5,158,548 | 10/1992 | Lau et al. . |
| 5,176,617 | 1/1993 | Fischell et al. . |
| 5,176,661 | 1/1993 | Evard et al. . |
| 5,180,368 | 1/1993 | Garrison . |
| 5,195,971 | 3/1993 | Sirhan . |
| 5,199,939 | 4/1993 | Dake et al. . |
| 5,213,561 | 5/1993 | Weinstien et al. . |
| 5,226,889 | 7/1993 | Sheiban . |
| 5,242,396 | 9/1993 | Evard . |
| 5,242,399 | 9/1993 | Lau et al. . |
| 5,258,419 | 11/1993 | Rolando et al. . |
| 5,263,963 | 11/1993 | Garrison et al. . |
| 5,267,960 | 12/1993 | Hayman et al. . |
| 5,273,738 | 12/1993 | Matthews et al. . |
| 5,279,562 | 1/1994 | Sirhan et al. . |
| 5,282,781 | 2/1994 | Liprie . |
| 5,295,959 | 3/1994 | Gurbel et al. . |
| 5,295,960 | 3/1994 | Aliahmad et al. . |
| 5,295,995 | 3/1994 | Kleiman . |
| 5,300,281 | 4/1994 | McMillan et al. . |
| 5,302,168 | 4/1994 | Hess . |
| 5,306,246 | 4/1994 | Sahatjian et al. . |
| 5,308,356 | 5/1994 | Blackshear, Jr. et al. . |
| 5,320,824 | 6/1994 | Brodack et al. . |
| 5,334,154 | 8/1994 | Samson et al. . |
| 5,336,518 | 8/1994 | Narayanan et al. . |
| 5,344,426 | 9/1994 | Lau et al. . |
| 5,350,361 | 9/1994 | Tsukashima et al. . |
| 5,352,199 | 10/1994 | Tower . |
| 5,354,257 | 10/1994 | Roubin et al. . |
| 5,360,401 | 11/1994 | Turnland et al. . |
| 5,380,747 | 1/1995 | Medford et al. . |
| 5,395,333 | 3/1995 | Brill . |
| 5,405,622 | 4/1995 | Vernice et al. . |
| 5,409,495 | 4/1995 | Osborn . |
| 5,411,466 | 5/1995 | Hess . |
| 5,415,664 | 5/1995 | Pinchuk . |
| 5,421,955 | 6/1995 | Lau et al. . |
| 5,441,516 | 8/1995 | Wang et al. . |
| 5,447,497 | 9/1995 | Sogard et al. . |
| 5,456,667 | 10/1995 | Ham et al. . |
| 5,458,572 | 10/1995 | Campbell et al. . |
| 5,484,384 | 1/1996 | Fearnot . |
| 5,498,227 | 3/1996 | Mawad . |
| 5,503,613 | 4/1996 | Weinberger . |
| 5,503,614 | 4/1996 | Liprie . |
| 5,507,301 | 4/1996 | Wasicek et al. . |
| 5,507,769 | 4/1996 | Marin et al. . |
| 5,514,154 | 5/1996 | Lau et al. . |
| 5,516,336 | 5/1996 | McInnes et al. . |
| 5,540,659 | 7/1996 | Teirstein . |
| 5,542,925 | 8/1996 | Orth . |
| 5,569,197 * | 10/1996 | Helmus et al. ......................... 604/96 |
| 5,569,295 | 10/1996 | Lam . |
| 5,573,508 | 11/1996 | Thornton . |
| 5,573,509 | 11/1996 | Thornton . |
| 5,616,114 | 4/1997 | Thornton et al. . |
| 5,618,266 | 4/1997 | Liprie . |
| 5,643,171 | 7/1997 | Bradshaw et al. . |
| 5,653,691 | 8/1997 | Rupp et al. . |
| 5,683,345 | 11/1997 | Waksman et al. . |
| 5,688,486 | 11/1997 | Watson et al. . |
| 5,707,332 | 1/1998 | Weinberger . |
| 5,720,717 * | 2/1998 | D'Andrea ............................ 604/21 |
| 5,730,698 | 3/1998 | Fischell et al. . |
| 5,782,740 | 7/1998 | Schneiderman . |
| 5,840,067 | 11/1998 | Berguer et al. . |
| 5,851,171 | 12/1998 | Gasson . |
| 5,871,436 | 2/1999 | Eury . |
| 5,910,101 | 6/1999 | Andrews et al. . |
| 5,938,582 | 8/1999 | Ciamacco, Jr. et al. . |
| 5,997,462 * | 12/1999 | Loffler ..................................... 600/3 |

FOREIGN PATENT DOCUMENTS

| | | |
|---|---|---|
| 0801961 | 4/1997 | (EP) . |
| 0829271 | 9/1997 | (EP) . |
| 0865803 | 3/1998 | (EP) . |
| 0879614 | 5/1998 | (EP) . |
| WO 92/17236 | 3/1992 | (WO) . |
| WO 93/04735 | 9/1992 | (WO) . |
| WO 94/25106 | 5/1994 | (WO) . |
| WO 94/25106 | 11/1994 | (WO) . |
| WO 95/19807 | 1/1995 | (WO) . |
| WO 95/26681 | 3/1995 | (WO) . |
| WO 96/06654 | 8/1995 | (WO) . |
| WO 96/10436 | 9/1995 | (WO) . |
| WO 96/14898 | 11/1995 | (WO) . |
| WO 96/19255 | 12/1995 | (WO) . |
| WO 96/19255 | 6/1996 | (WO) . |
| WO 97/07740 | 8/1996 | (WO) . |
| WO 97/37715 | 4/1997 | (WO) . |
| WO 97/40889 | 4/1997 | (WO) . |
| WO 98/01182 | 5/1997 | (WO) . |
| WO 98/01183 | 7/1997 | (WO) . |
| WO 98/01184 | 7/1997 | (WO) . |
| WO 98/01185 | 7/1997 | (WO) . |
| WO 98/39052 | 1/1998 | (WO) . |

OTHER PUBLICATIONS

Paul Jack Hoopes, D.V.M., Ph.D. et al., "Intraoperative Irradiation of the Canine Abdominal Aorta and Vena Cava", Int. J. Radiation Oncology Biol. Phys. vol. 13, pp 715–722, May 1987.

John T. Dawson, Jr, M.D., "Theoretic Considerations Regarding Low–Dose Radiation Therapy", Texas Heart Institute Journal, vol. 18, No. 1, pp 4–7, 1991.

Robert S. Schwartz, M.D. et al. "Effect of External Beam Irradiaton on Neointimal Hyperplasia After Experimental Coronary Artery Injury", JACC Vol. 19, No. 5, pp 1106–1113, Apr. 1992.

Joseph G. Wiedermann, M.D. et al.,"Intracoronary Irradiation Markedly Reduces Restenosis After Balloon Angioplasty in a Porcine Model", JACC vol. 23, No. 6, pp 1491–1498, May 1994.

Tim A. Fischell, M.D. et al., "Low–Dose B–Particle Emission from 'Stent' Wire Resutls in Complete, Localized Inhibition of Smooth Muscle Cell Proliferation", Circulation, vol. 90, No. 6, pp 2956–2963, Dec. 1994.

Ron Waksman M.D. et al., "Endovascular Low–Dose Irradiation Inhibits Neointima Formation After Coronary Artery Balloon Injury in Swine", Circulation, vol. 91, No. 5, pp 1533–1539, Mar. 1, 1995.

Z. Weshler et al., "Inhibition by Irradiation of Smooth Muscle Cell Proliferation in the De–Endothelialized Rat Aorta", Frontiers in Radiation Biology, pp 133–138, Oct. 1988.

C. Hehrlein et al. "Radioactive Stents", Abstract 22, pp 63–64, Discoveries in Radiation for Restenosis, Jan. 1996.

Tim A. Fischell, M.D. et al., "A Beta–Particle Emitting Radioisotope Stent for The Prevention of Restenosis" Abstract 23, pp 65, Discoveries in Radiation for Restenosis, Jan. 1996.

Alexander N. Li et al., "A Novel Brachyehtapy Source for Treatment of Coronary Artery Restenosis", Abstract 24, pp 67–72, Discoveries in Radiation for Restenosis, Jan. 1996.

Ron Waksman, M.D., "Catheter–Based Radiation In Stented Arteries", Abstract 25, pp 73–74, Discoveries in Radiation for Restenosis, Jan. 1996.

Louis G. Martin, M.D., "Radiation for Peripheral Applications: Technical Aspects", Abstract 27, pp 81–82, Discoveries in Radiation for Restenosis, Jan. 1996.

Alan B. Lumsden, M.D. et al, "Restenosis in Peripheral Vascular Disease", Abstract 28, pp 83–88, Discoveries in Radiation for Restenosis, Jan. 1996.

B. Schopohl et al., "Endovascular Irradiation for Avoidance or Recurrent Stenosis After Stent Implantation in Peripheral Arteries–5 years Follow–up", Abstract 29, pp 89–92, Discoveries in Radiation for Restenosis, Jan. 1996.

pg,8

Ron Waksman, M.D., "Radiation in the Peripheral System at Emory", Abstract 30, pp 93–94, Discoveries in Radiation for Restenosis, Jan. 1996.

Paul S. Teirstein et al., "Catheter–Based Radiation Therapy to Inhibit Restenosis Following Coronary Stenting", Abstract 31, pp 99, Discoveries in Radiation for Restenosis, Jan. 1996.

Spencer B. King III, M.D., "Clinical Restenosis Trials Using Beta Energy Radiation", Abstract 32, pp 101–102, Discoveries in Radiation for Restenosis, Jan. 1996.

Philip Urban, M.D. et al., "Endovascular Irradiation with 90Y Wire", Abstract 33, pp 103–104, Discoveries in Radiation for Restenosis, Jan. 1996.

Jose A. Condado, et al., Late Follow–up After Percutaneous Transluminal Coronary Angioplasty (PTCA) and Intracoronary Radiation Therapy (ICRT), Abstract 34, pp 105, Jan. 1996.

Thomas D. Weldon, "Catheter Based Beta Radiation System", Abstract 35, pp 111, Discoveries in Radiation for Restenosis, Jan. 1996.

Eric Van't Hooft, et al., "HDR Afterloader for Vascular Use", Abstract 36, pp 113, Discoveries in Radiation for Restenosis, Jan. 1996.

Robert E. Fischell, et al., "The Radioisotope Stent: Conception and Implementation", Abstract 37, pp 115, Discoveries in Radiation for Restenosis, Jan. 1996.

Youri Popowski M.D., et al., "Radioactive Wire in a Self- –Centering Catheter System", Abstract 38, pp 117–118, Discoveries in Radiation for Restenosis, Jan. 1996.

Richard V. Calfee, Ph.D., "High Dose Rate Afterloader System For Endovascular Use–Neocardia", Abstract 39. pp 119, Discoveries in Radiation for Restenosis, Jan. 1996.

Dr. Edward F. Smith III, "Issues on Handling Radioactive Devices to Prevent Restenosis", Abstract 40, pp 121–122, Discoveries in Radiation for Restenosis, Jan. 1996.

Richard E. Kuntz, M.D. et al., "Generalized Model of Restenosis After Conventional Balloon Angioplasty, Stenting and Directional Atherectomy", JACC, vol. 21, No. 1, pp 15–25, Jan. 1993.

Robert S. Schwartz et al., "Differential Neointimal Response to Coronary Artery Injury in Pigs and Dogs", Arteriosclerosis and Thrombosis, vol. 14, No. 3, pp 395–400, Mar. 1994.

Michael Haude, M.D. et al, "Quantitative Analysis of Elastic Recoil after Balloon Angioplasty and After Intracoronary Implantation of Balloon–Expandable Palmaz–Schatz Stents", JACC vol. 21, No. 1, pp 26–34, Jan. 1993.

Tsunekazu Kakuta, M.D. et al., "Differences in Compensatory Vessel Enlargement, Not Intimal Formation, Account for Restenosis After Angioplasty in the Hypercholesterolemic Rabbit Model" Circulation vol. 89, No. 6, pp 2809–2815, Jun. 1994.

Christina Unterberg, M.D. et al., "Reduced Acute Thrombus Formation Results in Decreased Neointimal Proliferation After Coronary Angioplasty", JACC vol. 26, No. 7, pp. 1747–1754, Dec. 1995.

Roger W. Byhardt et al., "The Heart and Blood Vessels", Radiation Oncology:Rationale, Technique, Results, pp 277–284, Jan. 1996.

C.G. Soares et al., "Measurement of Radial Dose Distributions Around Small Beta Particle Emitters Using High Resolution Radiochromic Foil Dosimetry", Nuclear Technology Publishing vol. 4, No. 1, pp 367–372, 1992.

Ron Waksman M.D. et al., "Intracoronary Low–Dose B–Irradiation Inhibits Neointima Formation After Coronary Artery Balloon Injury in the Swine Restenosis Model", Circulation, vol. 92, No. 10, pp 3025–3031, Nov. 15, 1995.

Joseph G. Wiedermann, M.D. et al., "Intracoronary Irradiation Markedly Reduces Neointimal Proliferation After Balloon Angioplasty in Swine: Persistent Benefit at 6–month Follow–up", JACC vol. 25, No. 1, pp. 1451–1456, May 1995.

Joseph G. Widermann et al., "Effects of High Dose Intracoronary Irradiation on Vasomotor Function and Smooth Muscle Histopathology", Intracoronary Irradiation and Vasomotion, pp H125–H132, 1994.

Keith L. March, M.D. et al., "8–Methoxypsoralen and Longwave Ultraviolet Irradiation Are a Novel Antiproliferative Combination for Vascular Smooth Muscle", Circulation, vol. 87, No. 1, pp 184–191, Jan. 1993.

Vitali Verin, M.D., et al., "Intra–Arterial Beta Irradiation Prevents Neointimal Hyperplasia in a Hypercholesterolemic Rabbit Restenosis Model", Circulation, vol. 92, No. 8, pp 2284–2290, Oct. 15, 1995.

Ron Waksman M.D. et al., "Intracoronary Radiation Before Stent Implantation Inhibits Neointima Formation in Stented Porcine Coronary Arteries", Circulation, vol. 92, No. 6, pp 1383–1386, Sep. 15, 1995.

Chrisoph Hehrlein, M.D., et al., "Low–Dose Radioactive Endovascular Stents Prevent Smooth Muscle Cell Proliferation and Neointimal Hyperplasia in Rabbits", Circulation, vol. 92, No. 6, pp 1570–1575, Sep. 15, 1995.

Barry T. Katzen, M.D., "Mechanical Approaches to Restenosis in the Peripheral Circulation", Jan. 1996.

Dieter Liermann et al., "Prophylactic Endovascular Radiotherapy to Prevent Intimal Hyperplasia After Stent Implantation in Femoropoliteal Arteries", Cardiovascular and Interventional Radiology, vol. 17, pp 12–16, 1994.

Louis K. Wagner, PH.D. et al., "Potential Biological Effects Following High X-Ray Dose Intervational Procedures[1]", Journal of Vascular and Interventional Radiology, pp 71–84, Jan.–Feb. 1994.

Lewis W. Johnson et al., "Review of Radiation Safety in the Cardiac Catheterization Laboratory", Catheterization and Cardiovascular Diganosis, vol. 25, pp 186–194, 1992.

William S. Weintraub M.D. et al., "Can Restenosis After Coronary Angiplasty Be Predicted From Clinical Variables?", JACC vol. 21, No. 1, pp 6–14, Jan. 1993.

Maria G. M. Hunink, M.D., et al., "Risks and Benefits of Femoropopliteal Percutaneous Balloon Angiplasty", Journal of Vascular Surgery, vol. 17, No. 1, pp 183–194, Jan. 1993.

PCT Search Report PCT/US 99/03327 mailed Jun. 18, 1999.

PCT Search Report PCT/US 99/03343 mailed Jun. 17, 1999.

PCT Search Report PCT/US 99/03328 mailed Jun. 18, 1999.

PCT Search Report PCT/US 99/03329 mailed Jun. 18, 1999.

PCT Search Report PCT/US 99/03360 mailed Jun. 17, 1999.

U.S. Patent application No. 08/654,698, filed May 29, 1996, Loeffler, Radiation–Emitting Flow–Through Temporary Stent.

* cited by examiner

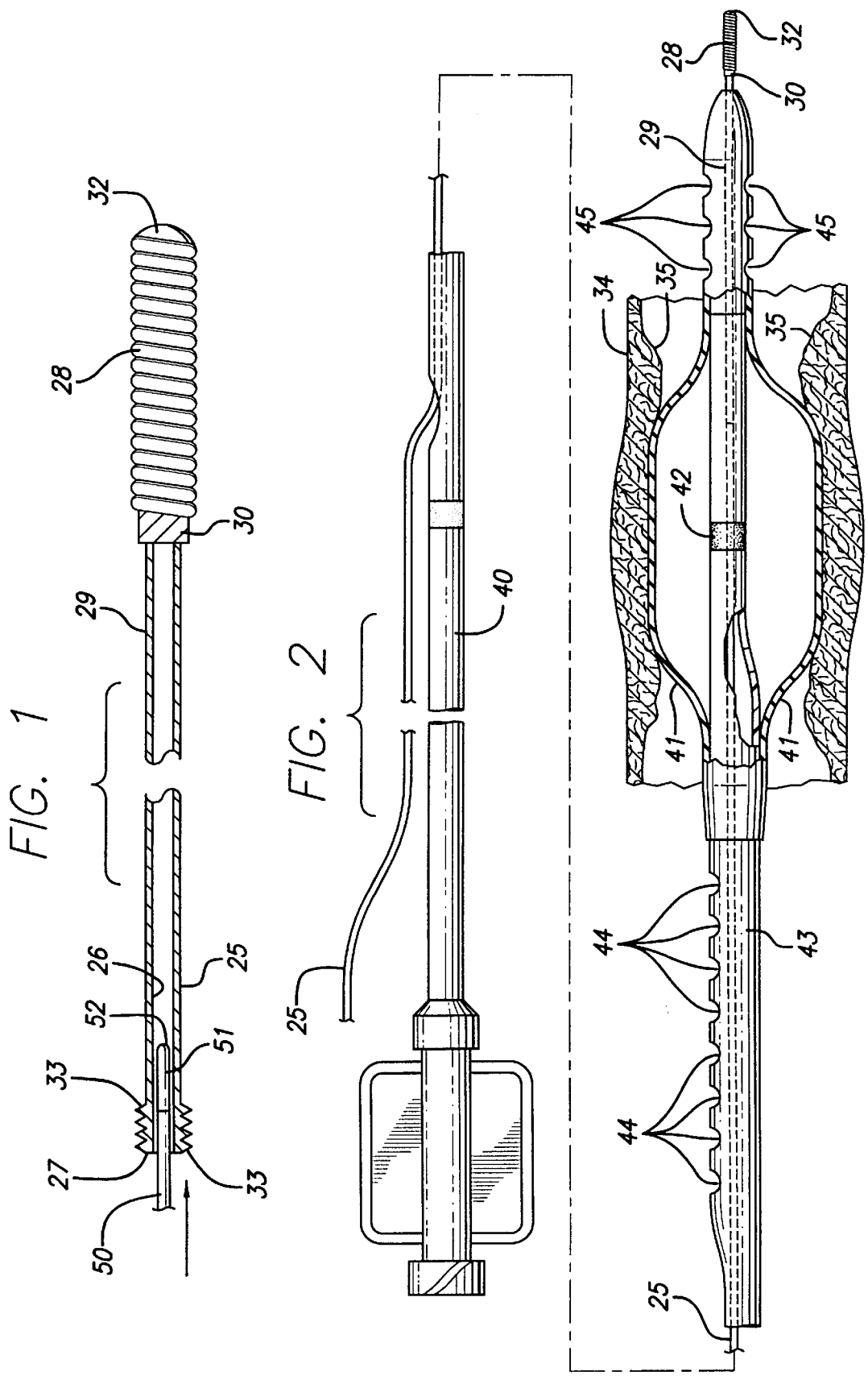

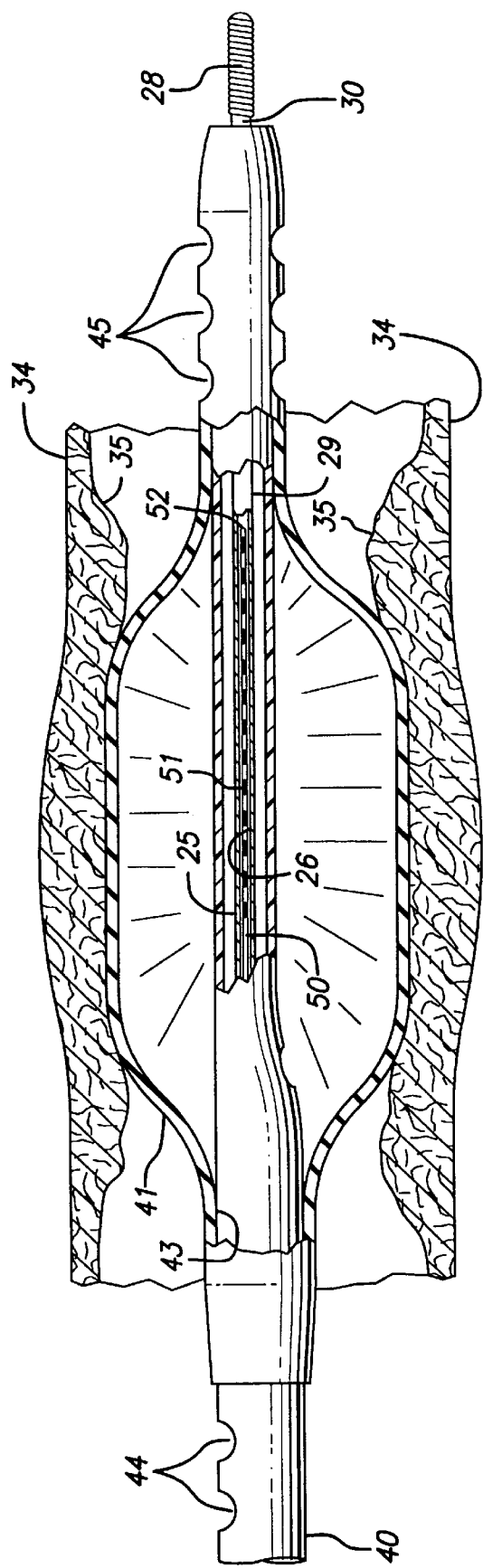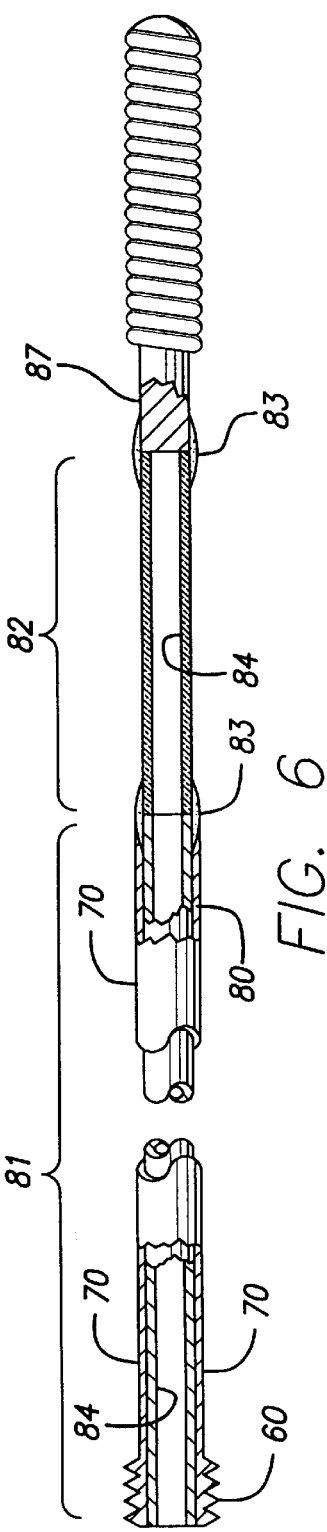

CATHETER AND GUIDE WIRE ASSEMBLY FOR DELIVERY OF A RADIATION SOURCE

BACKGROUND OF THE INVENTION

1. Field of the Invention

The present invention relates to an apparatus and method for reducing the likelihood of development of restenosis after arterial intervention, and more particularly to a hollow guide wire for delivery of a radioactive source to the site of the lesion following, or during, an intravascular procedure such as percutaneous transluminal coronary angioplasty (PTCA).

2. Description of the Prior Art

In PTCA procedures, a guiding catheter having a preshaped distal tip is percutaneously introduced into the cardiovascular system of a patient and advanced therein until the preshaped distal tip thereof is disposed within the aorta adjacent to the ostium of the desired coronary artery. The guiding catheter is twisted or torqued from the proximal end to turn the distal tip of the guiding catheter so that it can be guided into the coronary ostium. In an over-the-wire dilatation catheter system, a dilatation catheter having a balloon on its distal end and a guide wire slidably disposed within an inner lumen of the dilatation catheter are introduced into and advanced through the guiding catheter to its distal tip. The distal tip of the guide wire is usually manually shaped (i.e., curved) before the guide wire is introduced into the guiding catheter along with the dilatation catheter. The guide wire is usually first advanced out the distal tip of the guiding catheter, into the patient's coronary artery, and torque is applied to the proximal end of the guide wire, which extends out of the patient, to guide the curved or otherwise shaped distal end of the guide wire as the guide wire is advanced within the coronary anatomy until the distal end of the guide wire enters the desired artery. The advancement of the guide wire within the selected artery continues until its distal end crosses the lesion to be dilated. The dilatation catheter is then advanced out the distal tip of the guiding catheter, over the previously advanced guide wire, until the balloon on the distal extremity of the dilatation catheter is properly positioned across the lesion. Once properly positioned, the dilatation balloon is inflated to a predetermined size (preferably the same as the normal inner diameter of the artery at that particular location) with radiopaque liquid at relatively high pressures (e.g., 4–12 atmospheres) to dilate the stenosed region of the diseased artery. The balloon is then deflated so that the dilatation catheter can be removed from the dilated stenosis and blood flow can resume through the dilated artery.

A rapid exchange catheter has a relatively short guide wire-receiving sleeve or inner lumen (sometimes referred to as the "rail") extending a short distance through the distal portion of the catheter body. This inner lumen preferably extends approximately 10 cm, and typically about 30 to 40 cm, from a first guide wire port at the distal end of the catheter to a second side guide wire port located on the catheter body. In some catheters the rail can be much smaller than 10 cm, especially when the side guide wire port is located distal to the inflation balloon. The catheter can be advanced within the patient's vascular system in much the same fashion as described above as the short, guide wire lumen of the catheter slides along the length of the guide wire. Alternatively, the guide wire may be first advanced within the patient's vasculature until the distal end of the guide wire extends distally to the stenosis with the catheter then being mounted onto the proximal end of the in-place guide wire and advanced over the guide wire until the balloon portion is positioned across the stenosis. This particular structure allows for the rapid exchange of the catheter usually without the need for an exchange wire or adding a guide wire extension to the proximal end of the guide wire. Other over-the-wire or rapid exchange catheters can also be designed to utilize therapeutic or diagnostic means in place of the balloon in the description above.

Several notable improvements have recently been made in balloon angioplasty catheters. One such improvement is described in U.S. Pat. No. 4,748,982 (Horzewski et al.) wherein a short sleeve or inner lumen at least about 10 cm in length is provided within the distal section of the catheter body which extends from a first port proximal to the balloon to a second port in the distal end of the guide wire and which is adapted to slidably receive a guide wire. The proximal port is not less than about 10 cm and not more than about 40 cm from the distal end of the catheter. Preferably, a slit is provided in the catheter body extending from the proximal port to a location proximal to the proximal end of the balloon to facilitate the rapid removal of the catheter from the proximal end of the guide wire which extends out of the patient.

Another improvement, which was introduced into the market place by the assignee of the present application (Advanced Cardiovascular Systems, Inc.), has been perfusion-type dilatation catheters which allow for long term dilatations to repair arterial dissections and other arterial damage. These perfusion catheters have a plurality of perfusion ports in the wall forming at least part of the catheter body proximal to the balloon which are in fluid communication with an inner lumen extending to the distal end of the catheter body. A plurality of perfusion ports are preferably provided in the catheter body distal to the balloon which also are in fluid communication with the inner lumen extending to the distal end of the catheter body. When the balloon on the distal extremity of the dilatation catheter is inflated to dilate a stenosis, oxygenated blood in the artery or other vessel, depending upon the location of the dilatation catheter within the coronary anatomy, passes through the proximal perfusion ports, through the inner lumen of the catheter body and out the distal perfusion ports. This provides oxygenated blood downstream from the inflated balloon to thereby prevent or minimize ischemic conditions in tissue distal to the catheter to thereby facilitate long term dilatations. As is appreciated by those skilled in the art, tissue distal to a stenosis is frequently already in jeopardy due to ischemic conditions which may exist. As a result, care should be exercised in sizing the perfusion ports and the inner lumen to ensure that there is adequate flow of oxygenated blood to tissue distal to the catheter to eliminate or minimize ischemic conditions. Unfortunately, commercially available perfusion catheters have relatively large profiles due to the size of the inner tubular member which extends through the interior of the balloon and which prevents their use in many distal coronary locations.

A major and continual thrust of development work in the field of intravascular catheters, particularly coronary angioplasty catheters, has been to reduce the profile, i.e. transverse dimensions, of such catheters and to improve the flexibility thereof without detrimentally affecting their "pushability," particularly in the distal portion of such catheters. A reduction in profile with little or no loss in pushability allows a dilatation catheter to be advanced much further into a patient's coronary vasculature and to cross much tighter lesions.

The guide wires employed in coronary angioplasty are of relatively small diameter because of the relatively small size of the blood vessels and the luminal openings of the dilatation catheters which pass over the guide wires. To facilitate steering or placement within the cardiovascular system, a guide wire should be both relatively flexible toward its distal end and relatively rigid from a torsional standpoint over its entire length (i.e. it should possess "pushability" and "torqueability"). These two desirable properties are somewhat inconsistent and difficult to achieve in practice.

While guide wires designed for coronary angioplasty can, at least in theory, also be employed in the peripheral organs such as the arms and the legs, they may not have sufficient torsional rigidity for use in such applications. In addition, it is difficult to track a catheter with a relatively large luminal opening over a guide wire of relatively small diameter to a desired location. Ideally, the guide wire should fit closely within the luminal opening and loosely enough to permit the catheter to move freely along the wire.

Further details of guiding catheters, dilatation catheters, guide wires, and other devices for angioplasty and other procedures can be found in U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson); U.S. Pat. No. 4,538,622 (Samson et al.); U.S. Pat. No. 4,554,929 (Samson et al.); U.S. Pat. No. 4,582,181 (Samson); U.S. Pat. No. 4,616,652 (Simpson); U.S. Pat. No. 4,638,805 (Powell); U.S. Pat. No. 4,748,986 (Morrison et al.); U.S. Pat. No. 4,898,577 (Badger et al.); and U.S. Pat. No. 4,827,941 (Taylor et al.), which are hereby incorporated herein in their entirety by reference thereto.

A common problem that sometimes occurs after an angioplasty procedure has been performed is the development of restenosis at, or near, the original site of the stenosis. When restenosis occurs, a second angioplasty procedure or even bypass surgery may be required, depending upon the degree of restenosis. It is currently estimated that approximately one third of patients undergoing PTCA procedures develop restenosis within six months. In order to prevent this occurrence and thus obviate the need to perform bypass surgery or subsequent angioplasty procedures, various devices and procedures have been developed for reducing the likelihood of development of restenosis after arterial intervention. For example, an expandable tube (commonly termed a "stent") designed for long term implantation within the body lumen has been utilized to help prevent restenosis. By way of example, several stent devices and stent delivery systems can be found in commonly assigned and commonly owned U.S. Pat. No. 5,158,548 (Lau et al.); U.S. Pat. No. 5,242,399 (Lau et al.); U.S. Pat. No. 5,344,426 (Lau et al.); U.S. Pat. No. 5,421,955 (Lau et al.); U.S. Pat. No. 5,514,154 (Lau et al.); U.S. Pat. No. 5,569,295 (Lam); and U.S. Pat. No. 5,360,401 (Turnlund et al.), which are hereby incorporated herein in their entirety by reference thereto.

More recent devices and procedures for preventing restenosis after arterial intervention employ the use of a radiation source to minimize or destroy proliferating cells which are thought to be a major factor in restenosis development. Balloon catheters have been suggested as a means to deliver and maintain the radiation source in the area where arterial intervention has taken place, exposing the area to a sufficient radiation dose to abate cell proliferation. Two such devices and methods are described in U.S. Pat. No. 5,302,168 (Hess) and U.S. Pat. No. 5,503,613 (Weinberger). Other devices and methods which utilize radiation treatment delivered by an intravascular catheter are disclosed in commonly assigned and commonly owned co-pending U.S. Ser. No. 08/654,698, filed May 29, 1996, entitled Radiation-Emitting Flow-Through Temporary Stent, which is hereby incorporated herein by reference thereto.

Another medical device for the treatment of a body lumen by radiation is disclosed in European Patent App. No. 0 688 580A1 (Schneider). In the Schneider device, the balloon catheter includes a lumen that extends from a proximal opening to an area near the distal end of the catheter, where it dead ends. This lumen, known as a "blind" or "dead end" lumen, is intended to carry a radioactive tipped source wire that slides into the lumen once the catheter is in place in the artery or body lumen. When the source wire is positioned, the radioactive section at the distal tip lies near the dead end to provide radiation to the body lumen.

Another procedure employed to deliver a radiation source to a vessel is disclosed in U.S. Pat. No. 5,503,613 (Weinberger), wherein a catheter is provided with two inner lumens. One lumen accepts a guide wire for sliding into the body lumen. The other lumen is a blind lumen and receives a radiation dose delivery wire manipulated remotely by a computer controlled afterloader. After the catheter has been positioned with its distal end lying just past the stenosed area, the radiation dose delivery wire is inserted into the open end of the blind lumen and advanced to the dead end where it delivers a radiation dose to the affected tissue. This method necessitates a rather large catheter cross section to accommodate both lumens, which can complicate the insertion of the catheter in narrow, tortuous arteries. Another method bypasses this problem by employing an over-the-wire catheter to treat the stenosed region, then withdrawing the guide wire and inserting the radiation dose delivery wire in its place. Unfortunately, with this latter device, the radiation source wire will be exposed to blood, requiring sterilization if reuse is contemplated, or disposal after one use, which is costly and presents radioactive waste disposal issues.

The use of nuclear radiation to prevent restenosis represents a significant improvement in the safety and success rate of PTCA and percutaneous transluminal angioplasty (PTA) procedures. However, a few attendant factors give rise to special considerations that must be addressed to successfully employ this method. In particular, withdrawing the guide wire is disfavored by physicians because it results in a more complex and lengthy procedure, thereby increasing the risk of complications. Furthermore, if the radiation source delivery wire comes in direct contact with the patient's blood, it can cause blood contamination requiring that the radiation wire be sterilized before it is retracted into the afterloader and used on another patient. In addition, the salts and other chemical compounds found in blood may adversely impact the radiation source delivery wire and shorten its useful life.

Another consideration peculiar to intraluminal radiation therapy is that the radiation source must be located centrally within the body lumen being treated to assure uniform delivery of the radiation dose to the entire target area. Typically the radioactive sources employed are gamma ray emitters, and point source gamma rays attenuate inversely with the square of the distance traveled. If the radiation dose delivery wire lies closer to one side of the lumen or at an angle to it, the radiation dose delivered will be nonuniform along the entire length of the target area and some areas can receive appreciably larger doses than others. Achieving such precise spatial alignment of the radiation dose delivery wire is difficult in practice. Although this problem is not encountered when the radiation source is embedded in the tip of the catheter, which is usually centered within the lumen by the inflated balloon, the use of catheters to deliver the radiation dose can result in increased radiation doses being delivered to the body lumens leading to the stenosed area due to the longer insertion time required for catheters. In addition, repeated insertion and withdrawal of catheters can cause additional damage to vascular tissue due to their relatively large cross section.

Despite many advances in the field, there remains the need for an apparatus that will minimize the time required to accurately deliver a radiation source to a body lumen following an intravascular intervention such as PTCA and that will eliminate the exposure of the radioactive source material to the blood stream. Such a device will ideally combine the best features of both catheters and radiation source delivery wires into one novel and effective package that will further enhance the safety and success rate of intravascular procedures.

SUMMARY OF THE INVENTION

The present invention provides for an apparatus and method of treating a body lumen, such as a coronary artery or other artery or vein, with radiation to reduce the likelihood of the development of restenosis. In keeping with the invention, a guide wire is provided that is adapted to receive a radiation source for delivery to a target area in the body lumen. Typically, the radiation source will be delivered through a lumen in the guide wire to irradiate the target area. The term "target area" as used herein means that portion of a body lumen that is to receive a radiation dose.

The present invention provides a hollow guide wire having proximal and distal ends, a radiation source lumen extending from the proximal end to a point proximate the distal end, and a solid core portion at the distal end. A flexible tip may be secured to the solid core portion to facilitate inserting and navigating the guide wire through tortuous body lumens. The radiation source lumen is adapted to concentrically and slidably receive a radiation source delivery wire and the solid core portion defines the maximum distance the radiation source wire can be inserted in the radiation source lumen. Radiopaque markers may be provided on the outer surface of the hollow guide wire to assist in the precise positioning of the solid core portion and thus ensure accurate positioning of the radiation source wire relative to the target area.

The present invention includes an assembly for delivering the radiation source within a body lumen to the target area. The hollow guide wire having the radiation source lumen extending from the proximal end of the guide wire through to a point proximal to the distal end has a solid core portion proximate the distal end. A catheter is provided having a guide wire lumen which extends through at least a portion of the guide wire, the guide wire lumen being sized for receiving the guide wire. The guide wire lumen will extend through the catheter for over-the-wire applications, and will extend from a side port on the outer surface of the catheter through the distal end in rapid exchange catheter applications. An expandable member, such as a dilatation balloon, is associated with the distal end of the catheter for centering the guide wire within the body lumen, such as a coronary artery. A radiation source, such as a radiation source wire, is received in the radiation source lumen, and the radioactive portion of the radiation source wire is positioned proximate the distal end of the guide wire with the solid core portion of the guide wire defining the distal-most extent to which the radiation source can be advanced. The radiation source should be positioned within the radiation source lumen concentric with the balloon portion of the catheter, which is positioned at the target area to deliver the radiation dose thereto.

The method for irradiating the target area includes the assembly described for delivering a radiation dose within the body lumen. The guide wire is advanced within the body lumen such that the tip of the guide wire is advanced distal to the target area. The catheter is advanced over the guide wire so that the expandable member or balloon is positioned within the target area, so that the balloon portion of the catheter can be inflated into contact with the target area, thereby centering the guide wire and radiation source lumen within the target area. The radiation source, such as a radiation source wire, is advanced within the radiation source lumen of the guide wire so that a radioactive isotope can be positioned within the target area, to deliver a radiation dose thereto. After treatment, the radiation source is withdrawn from the radiation source lumen, the balloon portion of the catheter and guide wire are deflated and the catheter is withdrawn from the body lumen.

In either an over-the-wire or rapid exchange catheter application, it is contemplated that perfusion holes proximal and distal to the balloon portion of the catheters are provided to perfuse blood during the irradiating process.

The radiation therapy can be provided either during a PTCA or PTA procedure, or immediately thereafter. While it is contemplated that the target area can be irradiated prior to a dilatation procedure, it is not the preferred method. Preferably, a dilatation procedure such as a PTCA or PTA procedure is completed, and without withdrawing either the dilatation catheter or the guide wire, the irradiation procedure is accomplished as described.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 is a longitudinal cross-sectional view of the tubular guide wire and a position of the radiation source delivery wire embodying features of the present invention.

FIG. 2 is an elevational view, partially in section, depicting a rapid exchange catheter receiving the tubular guide wire shown in FIG. 1.

FIG. 5 is an enlarged cross-sectional view of the distal end of the catheter depicting the guide wire and the radiation source wire positioned at the target area to irradiate the area.

FIG. 6 is a cross-sectional view of the guide wire where at least a portion of the distal end of the guide wire is formed of a radiation transparent material such as a polymer.

DETAILED DESCRIPTION OF THE PREFERRED EMBODIMENTS

Figure 3:
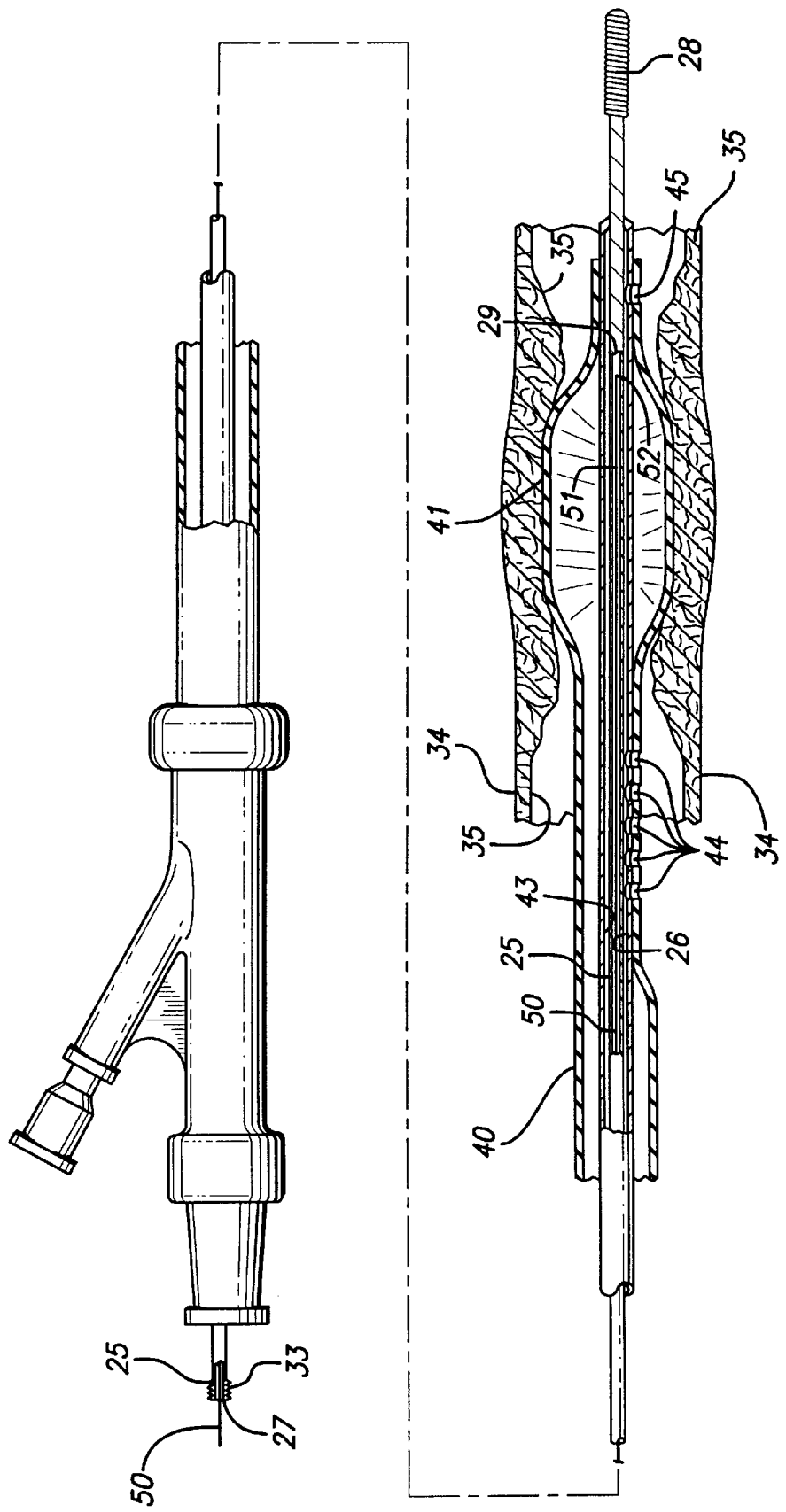
FIG. 3 is an elevational view, partially in section, depicting an over-the-wire catheter receiving the tubular guide wire and the radiation source wire inserted within the guide wire.

Intravascular procedures such as percutaneous transluminal coronary angioplasty (PTCA) or percutaneous transluminal angioplasty (PTA) sometimes result in development of restenosis in the treated or target area. A promising new technology that has been successfully used to prevent development of restenosis delivers a preselected dose of nuclear radiation to the target area during or immediately following the angioplasty procedure. The radiation dose is usually delivered via a wire incorporating radioactive source material that is inserted into the catheter used to treat the stenosed area. This procedure requires that the guide wire be first withdrawn from the catheter to permit insertion of the radiation dose delivery wire in the guide wire lumen in the catheter, or that the catheter incorporate an additional lumen that receives the radiation dose delivery wire. Such dual lumen catheters have higher profiles which are undesirable.

Referring to FIG. 1, in general, the present invention obviates the need for a dual lumen catheter or for removing the guide wire prior to radiation treatment by providing, generally, a tubular guide wire 25 formed with radiation source lumen 26 extending through a portion of the guide wire. The guide wire 25 has an opening at proximal end 27 for slidable receipt of radiation source wire 50, and formed at distal end 29 is flexible tip 28 used to navigate tortuous vessels.

Referring to FIG. 1, guide wire 25 may be formed from any high tensile strength material such as stainless steel, titanium, or a suitable superelastic nickel-titanium (NiTi) alloy, and may be formed through methods such as multiple extrusion of a tube through repeatedly smaller dies until the desired dimensions are achieved. It is important that the guide wire thus formed provide the critical characteristics of "pushability" and "torqueability" that allow it to be pushed along tortuous paths defined by the body lumens in which it is intended to be used.

If the guide wire is formed from NiTi, the preferred superelastic alloy has a final austenite transformation temperature ($A_f$) of less than about 40° C. and contains about 32 to about 52% titanium and the balance nickel and up to 10% additional alloying elements. A nickel content exceeding 50% causes brittleness and prevents effective cold working. The additional alloying elements may include iron, cobalt, chromium, platinum, palladium, tungsten, vanadium, copper and beryllium.

Alternatively, guide wire 25 may be constructed of a polymer or composite distal portion secured to a metal alloy proximal portion by any suitable method such as welding, brazing, or use of epoxies. Such construction would combine the "pushability" and "torqueability" characteristics of metal over substantially the length of the guide wire, with the flexibility inherent to polymers at its distal extremity, thereby facilitating the insertion and positioning of the guide wire within the patient's vascular system.

Guide wire 25 has a suitable outer diameter in the range of 0.008 to 0.032 inches and preferably an outer diameter of approximately 0.014 inches. A 0.014 inches outer diameter guide wire is compatible with most dilatation catheters presently on the market. Guide wire 25 shown in FIG. 1 has a constant outer diameter along its entire length, but it will be understood by those skilled in the art that guide wire 25 also may be formed in a tapering configuration having a larger outer diameter at proximal end 27 and a smaller diameter at distal end 29. The overall length of guide wire 25 can be in the range from 50 to 250 centimeters, and for coronary applications is preferably approximately 175 centimeters long. The guide wire may also be provided with radiation shielding means if the radioactive source material to be used warrants it. The radiation shield may be comprised of a flexible metal covering (not shown) encasing guide wire 25 to a point near the solid distal end, thereby defining a short window through which radiation can emit forth into the surrounding tissue. Such a metal covering may be of tubular construction or, alternatively, may be comprised of a coating around the guide wire.

Alternatively, a guide wire constructed of two materials, as will be described herein, could obviate the need for a separate radiation shield, and the metal alloy portion of the guide wire could be formed of sufficient thickness to act as the radiation shield while the distal polymer portion would provide a penetrable window for the emitted radiation.

The inner diameter of guide wire 25, namely radiation source lumen 26, will vary depending upon the intended application and the degree of flexibility required, as well as the outer diameter of guide wire 25. It is well known that the section modulus of a tube, defined as the measure of the capacity of a section of the tube to resist any bending moment applied to it, decreases with the thickness of the tube wall. A ratio of guide wire lumen diameter to outer diameter of 0.32, for example, will result in a decrease in section modulus of approximately one percent as compared to a solid tube, for example of the type used for conventional guide wires for use in PTCA and PTA procedures. The section modulus of a tube having a solid core varies with the cube of its diameter, and for this reason a larger diameter tubular guide wire can be formed with a larger lumen and yet provide the same section modulus as a smaller guide wire having a smaller lumen. In a preferred embodiment, guide wire 25 has an outer diameter of 0.014 inches and radiation source lumen 26 has a diameter that is preferably in the range of about 0.0045 to 0.010 inches.

The guide wire has solid core portion 30 at distal end 29 of the guide wire, which may be formed contiguous to the hollow portion (lumen 26) of the guide wire during the extrusion process, or may be attached to the hollow portion by any secure means such as welding, brazing, or the use of an epoxy. The method used should achieve a bond with a section modulus substantially equal to that of the guide wire hollow portion to prevent separation of solid core portion 30 while in the patient. The solid core portion includes flexible tip 28 to aid navigating the guide wire through tortuous body lumens. The flexible tip 28 may be attached to the solid portion by any suitable method or may be formed from the same core element such as by centerless grinding. One or more radiopaque markers 32 may be provided on guide wire 25 to allow the physician to see the position of guide wire distal end 29 on a fluoroscope. Alternatively, a portion of core 30 may be formed from a radiopaque material such as gold.

The proximal end 27 of guide wire 25 may be provided with fastening mechanism 33 such as a threaded fastener or similar mechanism for connecting guide wire 25 to a computer controlled afterloader (not shown). The fastening mechanism 33 will preferably be air and fluid tight, and will therefore be suited for use with solid, liquid or gaseous radioactive sources. The fastening mechanism 33 should also be rotatably mounted to the guide wire so that the circular position of the guide wire can be adjusted as necessary even after it has been connected to the afterloader. Alternatively, the fastening mechanism may be spring loaded, or a combination threaded/spring loaded assembly.

In operation, guide wire 25 is inserted into the patient's vascular system much in the same manner as conventional guide wires used in PTCA or PTA procedures. The flexible tip 28 at distal end 29 can be manually shaped by the physician into a selected configuration prior to insertion into the body lumen. The specially shaped tip 28 facilitates insertion and navigation of guide wire 25 through the body lumen, and radiopaque markers 32 allow the physician to track the location of the guide wire on a fluoroscope.

Figure 4:
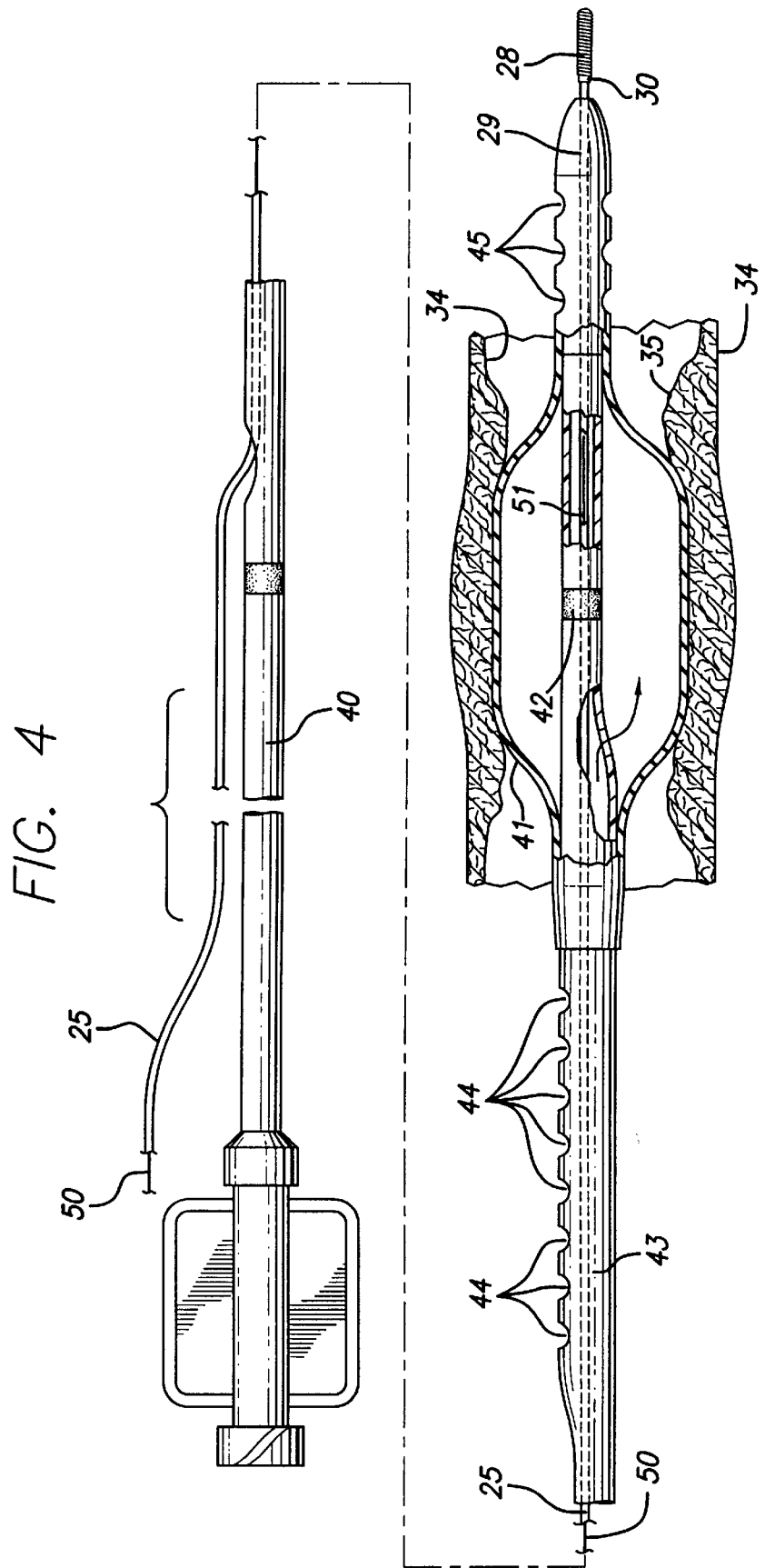
FIG. 4 is an elevational view, partially in section, depicting the rapid exchange catheter and guide wire of FIG. 2, where the guide wire has received the radiation source wire.

In conjunction with the guide wire of the invention, the preferred method of use is described. Referring to FIGS. 2, and 4–5, guide wire 25 is advanced in an artery 34 until distal end 29 is located just past the stenosed area, as is known in the art. Dilatation catheter 40 is advanced distally over guide wire 25 until inflatable balloon 41 of the catheter is positioned across the stenosed or target area 35. A radiopaque marker 42 is usually provided on the catheter at the midpoint of the inflatable balloon to aid the physician in tracking the progress of the catheter within the body lumen and to position the balloon within target area 35. Catheter 40 includes guide wire lumen 43 which is sized to slidably receive guide wire 25 and maintain it in a coaxial relationship thereto. Guide wire lumen 43 preferably is 0.001 to 0.002 inches larger than the outer diameter of the guide wire. Thus, in a preferred embodiment, guide wire 25 has an outer diameter of 0.014 inches, and guide wire lumen 43 preferably has an inner diameter of about 0.015 to 0.016 inches.

The dilatation catheter 40 is next used to treat the stenosis by inflating balloon 41 with a radiopaque liquid for a selected period of time. Catheter 40, shown in FIG. 2, is a rapid exchange catheter generally known in the art and has a plurality of perfusion ports 44 and 45, but it will be understood by those skilled in the art that the guide wire of the present invention works equally well with all other types of catheters including over-the-wire-type catheters. Thus, as seen in FIG. 3, the guide wire of the present invention is used with over-the-wire catheter 40 having perfusion capabilities. (Similar or like devices herein have the same reference numbers.) The guide wire of the present invention is uniquely well adapted for use with perfusion-type catheters because it allows insertion of the radioactive source without exposure to the patient's blood stream, thereby eliminating the risk of contaminating the blood stream or the wire. In extreme cases exposing the radiation source material to the blood of the patient may contaminate the blood and cause further complications for the patient. It is therefore highly desirable to provide the capability of isolating the blood stream from the radiation source while allowing blood flow through the body lumen being treated, two previously incompatible goals that are now achieved by the present invention.

Referring to FIGS. 1–5, following dilation of stenosed area 35, a radiation source, such as wire 50 having radioactive source material 51 formed in distal end 52, is inserted into proximal end 27 of radiation source lumen 26 and advanced therethrough adjacent to solid core portion 30 of guide wire 25. Solid core 30 limits the furthest extent to which radiation source wire 50 can be advanced distally into guide wire 25 through radiation source lumen 26, and because solid core portion 30 has been previously precisely located by the physician within the patient's artery by monitoring the location of radiopaque markers 32 on a fluoroscope, the physician can now determine with certainty the location of the radioactive source material 51 within the patient's body lumen.

The inflated balloon 41 pushes evenly against the walls of the artery and thus serves to center catheter 40 within artery 34, and thereby also centers guide wire 25, and radioactive source 51 within it. If the radiation source is in the form of wire 50, it should be of a suitable diameter to be slidably received and coaxially situated in the radiation source lumen 26, and is preferably about 0.001 to 0.002 inches smaller than the diameter of radiation source lumen. This is an important consideration in order to ensure that the radioactive source is centered within the body lumen so that the entire target area 34 receives an equal dose of radiation.

In oncology situations, radiation wires are typically inserted and advanced in the patient by a computer controlled afterloader, and the guide wire of the present invention is especially well suited for use with an afterloader. The proximal end 27 of guide wire 25, for instance, may be formed with fastener 33 adapted for connection to the afterloader (not shown) and thereby allowing completely hands-free insertion of radiation source wire 50. This would also allow precise positioning of the radiation source wire 50 because guide wire 25 is of a known length and the afterloader computer can thus calculate the precise distance to which the radiation source wire must be advanced to position radioactive source material 51 at target area 35.

The hollow guide wire 25 of the present invention allows delivery of the radiation dose immediately following, or indeed even during the PTCA pr PTA procedure. Conventional guide wires must typically be removed to make room for insertion of a radiation source wire, or alternatively an additional lumen must be provided within the catheter to receive the radiation source wire, thereby increasing the catheter profile. The task of exchanging wires is time consuming and may cause further complications, especially if a perfusion-type catheter is not employed and the patient's arteries are exposed to prolonged ischemic conditions in tissue distal to the catheter. Furthermore, repeated insertion and removal of guide wires increases the risk of traumatically engaging a vessel wall and, in a perfusion-type catheter, the risk of inserting one of wires in one of the perfusion ports. It is therefore desirable to minimize the amount of movement that the guide wire is subjected to once it has been properly positioned, as provided for by the guide wire of the present invention. This is also beneficial to provide a system having a single lumen catheter and thereby avoid the expense and complication of manufacturing a multiple lumen catheter which might, because of its construction, exhibit increased profile and increased stiffness resistant to easily following the circuitous path through a tortuous body lumen and be more likely to cause damage.

In one preferred method of use, radiation source wire 50 also may be positioned within guide wire 25 concurrent with the inflation of catheter balloon 41, thereby greatly reducing the total time required for performing the PTCA procedure. In this method, catheter 40 and guide wire 25 are advanced and positioned in artery 34 in the conventional manner for a PTCA procedure. Proximal end 27 of guide wire 25 is connected to an afterloader using fastener 33 or a similar connector. Radiation source wire 50 is advanced by the computer controlled afterloader into radiation source lumen 26 of guide wire 25. Since the distance from proximal end 27 of the guide wire to the center of balloon 41 is known, radiation source wire 50 is advanced until radioactive source material 51 is positioned within balloon 41. Simultaneous with balloon expansion to enlarge stenosed region 35, radioactive source material 51 will be emitting radiation at a predetermined rate and dose level. The guide wire remains in position for the entire procedure, which greatly reduces the overall time of the procedure and complications associated with the prior art devices. Radiation source wire 50 can be withdrawn into the afterloader when the predetermined dose level has been administered, which may be during or immediately after the PTCA procedure. It is contemplated that the guide wire of the present invention can be used with the radiation source wire to irradiate the target area before the PTCA procedure, however, there is little data at present that would suggest the benefit of such a procedure.

Guide wire 25 also can be employed solely as a radioactive dose delivery means in situations that do not require the insertion of a catheter. In such situations, guide wire 25 would act as a catheter, but with much reduced risk of damage to the body lumens and much enhanced ease of insertion and navigation within the lumens.

Referring to FIGS. 1 and 3–5, the radiation source has been illustrated as being in the form of wire 50. It will be understood by those skilled in the art, however, that guide wire 25 of the present invention is equally well suited for use with radioactive source materials that are gases, liquids, or slurries of solid particles suspended in solution. This is possible due to the guide wire's monolithic construction which provides lumen 26 presenting minimal risk of leaks developing and radioactive source materials leaking out or blood leaking in. A guide wire according to the present invention can thus be fastened in a leak-proof manner to an afterloader and the afterloader can then evacuate lumen 26 and discharge a radioactive liquid or gas into guide wire 25 for a predetermined period of time. This method could necessitate the use of a radiation shield 70 (FIG. 6) around guide wire 25, to prevent irradiating healthy tissue or catheter laboratory personnel.

Referring to FIG. 6, an alternative embodiment of the invention is shown in which guide wire 80 is formed of a radiation opaque metal alloy at proximal end section 81, while distal end section 82 is formed of a polymer that is substantially transparent to radiation. Distal end section 82 can be attached to proximal end section 81 by any suitable known means such as by adhesive bonding, laser welding, or the like. Annular bond 83 should ensure a secure connection between proximal and distal end sections 81 and 82. Likewise, distal end section 82 is securely attached to solid core portion 87 by annular bond 83. As described for other embodiments, guide wire 80 includes radiation source lumen 84 having an inner diameter adapted for receiving a radiation source such as radiation source wire 50 (not shown). The distal end section 82, being formed from a radiation transparent polymer, will permit maximum radiation exposure to target area 35 (not shown) when radiation source material 51 (not shown) is positioned within distal end section 82. Proximal end section 81 is formed from, for example, stainless steel alloy or other conventional guide wire metal alloys that are radiation opaque, so that as radiation source material 51 (not shown) is advanced through guide wire 80, it will not penetrate the metal alloy of proximal end section 81. Proximal end section 81 thus protects the patient and medical personnel from radiation exposure, while distal end section 82 selectively permits radiation penetration to target area 35 (not shown). As described, radiation shield 70, in the form of a covering or jacket, can be applied to cover proximal end section 81 to further ensure no or inconsequential amounts of radiation penetrate the proximal end section. Distal end section 82 should have a length that is consistent with the length of the catheter balloon, typically 20 mm to 40 mm for most coronary applications, but the length can vary for different applications. The proximal end of guide wire 80 may be provided with fastening mechanism 60 such as a threaded fastener or similar mechanism for connecting guide wire 80 to a computer controlled afterloader (not shown).

While there are numerous radioactive sources available for use with the present invention, the following radioisotopes are preferred: Iridium 192; Sodium 22; Scandium 46; Manganese 54; Yttrium 88; Cerium 139; Cerium 141; Strontium 85; Cobalt 57; Cobalt 60; Cesium 134; Palladium 103; Gold 198; Niobium 95; Mercury 203; Iodine 125; and Iodine 131. While gamma radiation is preferred for use with the present invention, beta radiation also is contemplated, although it may not penetrate as well as gamma radiation through the guide wire.

From the foregoing, it will be appreciated that the present invention provides a guide wire for use in intravascular procedures that allows the delivery of a radiation source without the use of a high profile, dual lumen catheter or exposure of the radiation source to the blood stream, and greatly reduces the time required for performing all intravascular procedures that incorporate radiation treatment of the affected area. Those skilled in the art will recognize that the invention is suitable for all types of catheters used with guide wires and may be used in a variety of body lumens. The present invention advances the state of the art for intravascular procedures with versatility in the types of radioactive source materials that can be employed, flexibility in the range of possible applications, and safety to the patient and attending medical staff.

While particular embodiments of the invention have been illustrated and described, various modifications can be made without departing from the spirit and scope of the invention, and all such modifications and equivalents are intended to be covered.

What is claimed is:

1. An apparatus for positioning a radiation source in a body lumen, the apparatus comprising:
   a guide wire having a proximal end, a distal end, and a radiation source lumen extending from the proximal end through the guide wire to a point near the distal end, wherein the radiation source lumen is isolated from the body lumen;
   a solid core portion proximate to the distal end of the guide wire such that the solid core portion defines the distal extent to which the radiation source may be advanced into the radiation source lumen; and
   a flexible guide wire tip at the distal end of the guide wire for navigating through the body lumen.

2. The apparatus of claim 1, wherein the guide wire is tapered, the guide wire proximal end having a larger diameter than the guide wire distal end.

3. The apparatus of claim 1, wherein the guide wire further comprises a shield to shield the body lumen from the radiation emitted by the radiation source.

4. The apparatus of claim 3, wherein the shield includes a metallic cover disposed around a portion of the guide wire.

5. The apparatus of claim 1, wherein the guide wire has an outer diameter substantially in the range of 0.008 to 0.032 inches.

6. The apparatus of claim 5, wherein the radiation source lumen has an inner diameter substantially in the range of 0.0045 to 0.010 inches.

7. The apparatus of claim 6, wherein the ratio of the radiation source lumen inner diameter to the guide wire outer diameter is no greater than 0.32.

8. The apparatus of claim 1, wherein at least a portion of the guide wire is formed from a metal alloy selected from the group of metal alloys including stainless steel, nickel-titanium, titanium, tungsten, platinum, iron, cobalt, chromium, palladium, and copper-beryllium.

9. The apparatus of claim 1, wherein at least a portion of the guide wire is formed from a flexible polymer material.

10. The apparatus of claim 1, wherein the guide wire includes a distal section formed from a polymer material and attached contiguously to a proximal portion formed from a metal alloy selected from the group of metal alloys including stainless steel, nickel-titanium, titanium, tungsten, platinum, iron, cobalt, chromium, palladium, and copper-beryllium.

11. The apparatus of claim 1, wherein the guide wire is approximately 50 cm to 250 cm long.

12. The apparatus of claim 1, wherein the guide wire has radiopaque markers formed thereon for viewing on a fluoroscope.

13. The apparatus of claim 1, wherein the radiation source lumen is adapted for receiving a radiation source material formed from a solid material.

14. The apparatus of claim 13, wherein the radiation source lumen is adapted for coaxially receiving the radiation source associated with a radiation source wire.

15. The apparatus of claim 13, wherein the radiation source lumen is adapted for receiving a radiation source wire that is advanced within the radiation source lumen by a remote afterloader.

16. The apparatus of claim 15, wherein the guide wire proximal end is provided with a fastener for connecting to the afterloader.

17. The apparatus of claim 1, wherein the radiation source lumen is adapted for receiving a radiation source formed from a radioactive slurry material.

18. The apparatus of claim 1, wherein the radiation source lumen is adapted for receiving a radiation source formed from a radioactive liquid material.

19. The apparatus of claim 1, wherein the radiation source lumen is adapted for receiving the radiation source formed from a radioactive gaseous material.

20. An assembly for positioning a radiation dose within a body lumen, comprising:
- a guide wire having a proximal end, a distal end, and a radiation source lumen extending from the proximal end through the guide wire to a point proximate the distal end;
- a solid core portion proximate the distal end of the guide wire;
- a guide wire tip on the distal end of the guide wire for navigating through the body lumen;
- a catheter having a guide wire lumen extending through at least a portion thereof, the guide wire lumen sized for receiving the guide wire;
- a radiation source received in the radiation source lumen and positioned proximate the distal end of the guide wire with the solid core portion defining the most distal extent to which the radiation source is inserted into the radiation source lumen; and
- a balloon concentric about the catheter and inflatable to contact the walls of the body lumen and center the catheter and the radiation source within the body lumen.

21. The assembly of claim 20, wherein the catheter guide wire lumen and the guide wire are sized such that the guide wire is received concentrically within the catheter guide wire lumen.

22. The assembly of claim 21, wherein the guide wire has an outer diameter approximately 0.001 to 0.002 inches smaller than an inner diameter of the catheter guide wire lumen.

23. The assembly of claim 20, wherein the catheter is a rapid-exchange-type catheter.

24. The assembly of claim 20, wherein the catheter is an over-the-wire-type catheter.

25. The assembly of claim 20, wherein the catheter is a perfusion-type catheter.

26. The assembly of claim 20, wherein the guide wire is tapered, the guide wire proximal end having a larger outer diameter than the outer diameter of the guide wire distal end.

27. The assembly of claim 20, wherein the guide wire further comprises a shield to shield the body lumen from the radiation emitted by the radiation source.

28. The assembly of claim 27, wherein the shield includes a metallic cover disposed around a portion of the guide wire.

29. The assembly of claim 20, wherein the catheter further comprises a shield to shield the body lumen from the radiation emitted by the radiation source.

30. The assembly of claim 29, wherein the shield includes a metallic cover disposed around at least a portion of the catheter.

31. The assembly of claim 20, wherein the guide wire has an outer diameter substantially in the range of 0.008 to 0.032 inches.

32. The assembly of claim 31, wherein the radiation source lumen has an inner diameter substantially in the range of 0.0045 to 0.010 inches.

33. The assembly of claim 32, wherein the ratio of the radiation source lumen inner diameter to the guide wire outer diameter is no greater than 0.32.

34. The assembly of claim 20, wherein at least a portion of the guide wire is formed from a metal alloy selected from the group of metal alloys including stainless steel, nickel-titanium, titanium, tungsten, platinum, iron, cobalt, chromium, palladium, and copper-beryllium.

35. The assembly of claim 20, wherein at least a portion of the guide wire is formed from a flexible polymer material.

36. The assembly of claim 20, wherein the guide wire includes a distal section formed from a polymer material attached to a proximal section formed from a metal alloy selected from the group of metal alloys including stainless steel, nickel-titanium, titanium, tungsten, platinum, iron, cobalt, chromium, palladium, and copper-beryllium.

37. The assembly of claim 20, wherein the guide wire is approximately 50 cm to 250 cm long.

38. The assembly of claim 20, wherein the radiation source is formed from a radiation source material selected from the group of radiation source materials including a radioactive solid material, a radioactive liquid, a radioactive gas, and a radioactive slurry.

39. The assembly of claim 38, wherein the radiation source is associated with a radiation source wire adapted for receipt into the radiation source lumen of the guide wire.

40. The assembly of claim 39, wherein the radiation source wire has an outer diameter approximately 0.001 to 0.002 inches smaller than the inner diameter of the radiation source lumen of the guide wire.

41. The assembly of claim 20, wherein the radiation source comprises a radiosotope selected from the group of radioisotopes including Iridium 192, Sodium 22, Scandium 46, Manganese 54, Yttrium 88, Cerium 139, Cerium 141, Strontium 85, Cobalt 57, Cobalt 60, Cesium 134, Palladium 103, Gold 198, Niobium 95, Mercury 203, Iodine 125, and Iodine 131.

42. A method for irradiating a portion of a body lumen, the method comprising:
- providing an assembly having a catheter with an expandable member at a distal end and a guide wire lumen extending through at least a portion thereof, the guide wire lumen sized for receiving a guide wire therein, the guide wire having a proximal end, a distal end, and a radiation source lumen extending from the proximal end through the guide wire to a point proximate the distal end, and a solid core portion on the distal end of the guide wire;
- positioning the catheter and the guide wire in the body lumen;
- advancing the guide wire so that the guide wire distal end is positioned distal to a target area in the body lumen;
- advancing the catheter over the guide wire so that the expandable member is positioned within the target area and inflating the expandable member into contact with the body lumen;

advancing a radiation source within the radiation source lumen so that a radioactive isotope is positioned within the target area;

irradiating the target area for a predetermined time and predetermined radiation dose level;

withdrawing the radiation source from the radiation source lumen; and deflating the expandable member and withdrawing the catheter and guide wire from the body lumen.

43. The method of claim 42, wherein the step of providing a catheter includes any of a rapid exchange catheter, an over-the-wire catheter, a fixed wire catheter, or a perfusion catheter.

44. The method of claim 42, wherein the step of advancing the radiation source includes advancing a radiation source wire having a radiation source associated with a distal end of the wire so that as the wire is advanced in the radiation source lumen, the radiation source at the distal end of the wire will be positioned within the target area.

45. The method of claim 44, wherein the advancing step further comprises advancing the radiation source wire using an afterloader and the withdrawing step further includes withdrawing the radiation source wire using the afterloader.

46. An apparatus for positioning a radiation source in a body lumen, the apparatus comprising:

a guide wire having a proximal end, a distal end, and a radiation source lumen extending from the proximal end through the guide wire to a point near the distal end;

a solid core portion at the distal end of the guide wire;

a flexible guide wire tip at the distal end of the guide wire for navigating through the body lumen;

the radiation source lumen adapted for receiving the radiation source to be positioned proximate the distal end of the guide wire with the solid core portion defining the distal-extent to which the radiation source is advanced into the lumen; and a shield to shield the body lumen from the radiation emitted by the radiation source.

47. The apparatus of claim 46, wherein the shield includes a metallic cover disposed around a portion of the guide wire.

48. The apparatus of claim 46, wherein the guide wire is tapered, the guide wire proximal end having a larger diameter than the guide wire distal end.

49. The apparatus of claim 46, wherein the guide wire has an outer diameter substantially in the range of 0.008 to 0.032 inches.

50. The apparatus of claim 49, wherein the radiation source lumen has an inner diameter substantially in the range of 0.0045 to 0.010 inches.

51. The apparatus of claim 50, wherein the ratio of the radiation source lumen inner diameter to the guide wire outer diameter is no greater than 0.32.

52. The apparatus of claim 46, wherein at least a portion of the guide wire is formed from a metal alloy selected from the group of metal alloys including stainless steel, nickel-titanium, titanium, tungsten, platinum, iron, cobalt, chromium, palladium, and copper-beryllium.

53. The apparatus of claim 46, wherein at least a portion of the guide wire is formed from a flexible polymer material.

54. The apparatus of claim 46, wherein the guide wire includes a distal section formed from a polymer material and attached contiguously to a proximal portion formed from a metal alloy selected from the group of metal alloys including stainless steel, nickel-titanium, titanium, tungsten, platinum, iron, cobalt, chromium, palladium, and copper-beryllium.

55. The apparatus of claim 46, wherein the guide wire is approximately 50 cm to 250 cm long.

56. The apparatus of claim 46, wherein the guide wire has radiopaque markers formed thereon for viewing on a fluoroscope.

57. The apparatus of claim 46, wherein the radiation source lumen is adapted for receiving a radiation source material formed from a solid material.

58. The apparatus of claim 57, wherein the radiation source lumen is adapted for coaxially receiving the radiation source associated with a radiation source wire.

59. The apparatus of claim 58, wherein the radiation source wire has an outer diameter approximately 0.001 to 0.002 inches smaller than the inner diameter of the radiation source lumen of the guide wire.

60. The apparatus of claim 57, wherein the radiation source lumen is adapted for receiving a radiation source wire that is advanced within the radiation source lumen by a remote afterloader.

61. The apparatus of claim 60, wherein the guide wire proximal end is provided with a fastener for connecting to the afterloader.

62. The apparatus of claim 46, wherein the radiation source lumen is adapted for receiving the radiation source formed from a radioactive slurry material.

63. The apparatus of claim 46, wherein the radiation source lumen is adapted for receiving the radiation source formed from a radioactive liquid material.

64. The apparatus of claim 46, wherein the radiation source lumen is adapted for receiving the radiation source formed from a radioactive gaseous material.

65. The apparatus of claim 46, wherein the radiation source comprises a radioisotope selected from the group of radioisotopes including Iridium 192, Sodium 22, Scandium 46, Manganese 54, Yttrium 88, Cerium 139, Cerium 141, Strontium 85, Cobalt 57, Cobalt 60, Cesium 134, Palladium 103, Gold 198, Niobium 95, Mercury 203, Iodine 125, and Iodine 131.

66. An apparatus for positioning a radiation source in a body lumen, the apparatus comprising:

a guide wire having a proximal end, a distal end, and a radiation source lumen extending from the proximal end through the guide wire to a point near the distal end;

a solid core portion at the distal end of the guide wire;

a flexible guide wire tip at the distal end of the guide wire for navigating through the body lumen; and a fastener for connecting the proximal end of the guide wire to a remote afterloader;

the radiation source lumen adapted for receiving a radiation source wire to be positioned proximate the distal end of the guide wire with the solid core portion defining the distal extent to which the radiation source is advanced into the lumen, wherein the radiation source wire is advanced within the radiation source lumen by the remote afterloader.

67. The apparatus of claim 66, wherein the guide wire further comprises a shield to shield the body lumen from the radiation emitted by the radiation source.

68. The apparatus of claim 67, wherein the shield includes a metallic cover disposed around a portion of the guide wire.

69. The apparatus of claim 66, wherein the guide wire is tapered, the guide wire proximal end having a larger diameter than the guide wire distal end.

70. The apparatus of claim 66, wherein the guide wire has an outer diameter substantially in the range of 0.008 to 0.032 inches.

71. The apparatus of claim 70, wherein the radiation source lumen has an inner diameter substantially in the range of 0.0045 to 0.010 inches.

72. The apparatus of claim 71, wherein the ratio of the radiation source lumen inner diameter to the guide wire outer diameter is no greater than 0.32.

73. The apparatus of claim 66, wherein at least a portion of the guide wire is formed from a metal alloy selected from the group of metal alloys including stainless steel, nickel-titanium, titanium, tungsten, platinum, iron, cobalt, chromium, palladium, and copper-beryllium.

74. The apparatus of claim 66, wherein at least a portion of the guide wire is formed from a flexible polymer material.

75. The apparatus of claim 66, wherein the guide wire includes a distal section formed from a polymer material and attached contiguously to a proximal portion formed from a metal alloy selected from the group of metal alloys including stainless steel, nickel-titanium, titanium, tungsten, platinum, iron, cobalt, chromium, palladium, and copper-beryllium.

76. The apparatus of claim 66, wherein the guide wire is approximately 50 cm to 250 cm long.

77. The apparatus of claim 66, wherein the guide wire has radiopaque markers formed thereon for viewing on a fluoroscope.

78. The apparatus of claim 66, wherein the radiation source lumen is adapted for coaxially receiving the radiation source associated with a radiation source wire.

79. The apparatus of claim 66, wherein the radiation source is associated with a radiation source wire adapted for receipt into the radiation source lumen of the guide wire.

80. The apparatus of claim 79, wherein the radiation source wire has an outer diameter approximately 0.001 to 0.002 inches smaller than the inner diameter of the radiation source lumen of the guide wire.

81. The apparatus of claim 66, wherein the radiation source comprises a radioisotope selected from the group of radioisotopes including Iridium 192, Sodium 22, Scandium 46, Manganese 54, Yttrium 88, Cerium 139, Cerium 141, Strontium 85, Cobalt 57, Cobalt 60, Cesium 134, Palladium 103, Gold 198, Niobium 95, Mercury 203, Iodine 125, and Iodine 131.

* * * * *

UNITED STATES PATENT AND TRADEMARK OFFICE
CERTIFICATE OF CORRECTION

PATENT NO. : 6,210,312 B1
DATED : April 3, 2001
INVENTOR(S) : Nagy

It is certified that error appears in the above-identified patent and that said Letters Patent is hereby corrected as shown below:

Title page,
Item [56], References Cited, FOREIGN PATENT DOCUMENTS, "0 633 041", please delete date "1/1995" and insert -- 7/1993 --.
"5,213,561", please delete inventor name "Weinstien et al." and insert -- Weinstein et al. --; please delete the second occurrence of "WO 94/25106" dated "11/1994"; and please delete the second occurrence of "WO 96/19255" dated "6/1996".
OTHER PUBLICATIONS, please delete "pg. 8" cited between publications "B. Schopohl et al." and "Ron Waksman, M.D.".

Column 14,
Line 43, please delete "radiosotope" and insert -- radioisotope --.

Signed and Sealed this

Eleventh Day of November, 2003

JAMES E. ROGAN
*Director of the United States Patent and Trademark Office*